(12) United States Patent
Thaden et al.

(10) Patent No.: US 7,427,370 B2
(45) Date of Patent: Sep. 23, 2008

(54) METHOD FOR THE PRODUCTION OF GRIGNARD COMPOUNDS

(75) Inventors: Bettina Thaden, Eschweiler (DE); Heike Stollenwerk, Nideggen (DE); Uwe Krebber, Eupen (DE)

(73) Assignee: Grunenthal GmbH, Aachen (DE)

( * ) Notice: Subject to any disclaimer, the term of this patent is extended or adjusted under 35 U.S.C. 154(b) by 381 days.

(21) Appl. No.: 10/882,425

(22) Filed: Jul. 1, 2004

(65) Prior Publication Data

US 2004/0245657 A1 Dec. 9, 2004

Related U.S. Application Data

(63) Continuation of application No. PCT/EP02/14790, filed on Dec. 28, 2002.

(30) Foreign Application Priority Data

Apr. 1, 2002 (DE) ................. 102 00 149

(51) Int. Cl.
*C07F 3/02* (2006.01)
(52) U.S. Cl. .................. 260/665 G
(58) Field of Classification Search ......... 260/665 G
See application file for complete search history.

(56) References Cited

U.S. PATENT DOCUMENTS 3,892,782 A 7/1975 Buchi .................. 260/346
4,958,033 A 9/1990 Takisawa et al. .......... 549/59
5,321,791 A * 6/1994 Fauvarque et al. .......... 385/143

FOREIGN PATENT DOCUMENTS

DE 199 60 865 A1 6/2001
EP 0 755 715 A1 1/1997

OTHER PUBLICATIONS

Yu et al., A convenient approach to substituted 1-(1-alkenyl)cyclopropanols: a new preparation of 2,3-methanoamino acids, Tetrahedron Letters, 2000, 41 (33), 6399-6402.*
Gedye et al., The Rapid Synthesis of Organic Compounds in Microwave Ovens II, Can. J. Chem., 66, 1988, 17-26.*
Majetich et al., Journal of Microwave Power and Electromagnetic Energy, 30, 1, 1995, 27-45.*
Whittaker et al., Journal of Microwave Power and Electromagnetic Energy, 29, 4, 1994, 195-219.*
Gedye et al., The Rapid Synthesis of Organic Compounds in Microwave Ovens, Can. J. Chem. 69, 1991, 706-711.*
"Preparation of an Extremely Active Magnesium Slurry for Grignard Reagent Preparations by Metal Atom-Solvent Cocondensations", K.J. Klabunde et al., Journal of Organometallic Chemistry, vol. 71, No. 3, 1974, pp. 309-313.
"Magnesium Activation", Reuben D. Rieke et al., Handbook of Grignard Reagents, 1996, pp. 53-77.
"Mechanisms of Grignard Reagent Formation", John F. Garst et al., Grignard Reagent: New Developments, 2000, pp. 185-275.
"Preparation of Organomagnesium Compounds", pp. 21-71.
"29-Organometallics", vol. 92, 1980, p. 621.

* cited by examiner

Primary Examiner—Yvonne Eyler
Assistant Examiner—Chukwuma O Nwaonicha
(74) Attorney, Agent, or Firm—Norris, McLaughlin & Marcus PA

(57) ABSTRACT

The invention relates to a method for producing Grignard compounds, according to which magnesium is reacted in a suitable fluid reaction medium in a protective atmosphere with hologen-substituted organic compounds by means of microwave radiation.

34 Claims, No Drawings

METHOD FOR THE PRODUCTION OF GRIGNARD COMPOUNDS

Continuation of prior PCT application No.: PCT/EP02/14790, filed 28 Dec. 2002.

BACKGROUND OF THE INVENTION

1. Field of the Invention

The present invention relates to a process for the production of Grignard compounds, according to which magnesium is reacted in a suitable liquid reaction medium under a protective gas atmosphere with halosubstituted organic compounds with microwave irradiation.

Over the past few decades, organometallic compounds have proven to be an indispensable reaction component in the synthesis of organic compounds both in the laboratory and in large industrial scale production despite their sometimes high sensitivity to atmospheric oxygen and moisture.

2. Brief Description of Related Developments

Organomagnesium compounds, which also include so-called Grignard compounds, have gained particular significance. These Grignard compounds may be obtained by reacting magnesium with halosubstituted organic compounds under a protective gas atmosphere in a suitable reaction medium and comprise a strongly polarised magnesium-carbon bond, in which the carbon atom bears the negative charge density, see for example, "Grignard Reagents: New Developments", Herman G. Richey Jr., John Wiley and Sons Ltd, 2000, pages 185 to 275, "Organomagnesium Methods in Organic Synthesis", Basil J. Wakefield, Academic Press, London, 1995, pages 21 to 71 and "Handbook of Grignard Reagents", Gary S. Silverman, Philip E. Rakita, Marcel Dekker, Inc., New York, 1996, pages 53 to 77.

The Grignard compounds therefore readily react as nucleophilic reagents with electrophilic compounds with formation of a new carbon-carbon-bond and are thus suitable for synthesis of larger organic compounds from appropriate fragments.

In practice, the production of Grignard compounds frequently proves difficult, as the surface of the magnesium is conventionally passivated by a magnesium oxide layer, which markedly impairs or even prevents reaction of the magnesium with the halosubstituted organic compound.

Processes have therefore been developed to activate the surface of the magnesium. Examples are chemical activation by mineral acids, elemental iodine or and by lithium salts, together with physical activation by heating or by ultrasound treatment.

However, a disadvantage of these processes for activating the magnesium is that, due to the long reaction times and optionally the elevated reaction temperatures, undesired secondary products are often formed in addition to the desired Grignard compound, such as for example hydrocarbon compounds by the reaction of two halosubstituted organic compounds through Wurtz coupling.

These secondary reactions lead on the one hand to a reduction in the yield of the desired Grignard compound and thus also to a reduction in the yield of the derived product produced therefrom. On the other hand, these secondary reactions frequently also impair or prevent the use of Grignard compounds in a synthesis, since the subsequently necessary purification steps make the process uneconomic or cannot be performed at all due to small substance quantities, such as for example in the field of combinatorial chemistry.

SUMMARY OF THE INVENTION

The object of the present invention was accordingly to provide a process for the production of Grignard compounds, with which these compounds are obtained within short reaction times and in high yields. Moreover, the obtained Grignard compounds should preferably also be distinguished by good to very good purity.

According to the invention, this object is achieved by a process for the production of at least one Grignard compound, by reacting magnesium in a suitable liquid reaction medium under a protective gas atmosphere with at least one halosubstituted organic compound, preferably a halosubstituted organic hydrocarbon compound, with microwave irradiation.

The magnesium is preferably used in the process according to the invention in strip form or in multiparticulate form, particularly preferably in the form of chips or powder. Very particularly preferably, the magnesium is used in the form of conventional, commercially obtainable chips.

Suitable reaction media which may be used are any reaction media known per se to the person skilled in the art for the production of Grignard compounds, as described for example in "Grignard Reagents: New Developments", Herman G. Richey Jr., John Wiley and Sons Ltd, 2000, pages 185 to 275, "Organomagnesium Methods in Organic Synthesis", Basil J. Wakefield, Academic Press, London, 1995, pages 21 to 71 and "Handbook of Grignard Reagents", Gary S. Silverman, Philip E. Rakita, Marcel Dekker, Inc., New York, 1996, pages 53 to 77. The corresponding literature descriptions are hereby introduced as a reference and are deemed to be part of the disclosure.

The reaction medium is preferably an ether compound or a mixture containing at least one ether compound. The ether compound is preferably selected from the group comprising aliphatic ethers, cyclic ethers and aliphatic polyethers. Mixtures of two or more representatives of one or more of the above-stated classes of ethers may also be used.

Examples of preferred aliphatic ethers are diethyl ether, dibutyl ether or mixtures thereof.

Preferred cyclic ethers are tetrahydrofuran, 1,4-dioxane or mixtures thereof.

Preferred aliphatic polyethers are based on alkylene glycols, such as for example ethylene glycol, and are particularly preferably selected from the group comprising ethylene glycol dimethyl ether (monoglyme), diethylene glycol dimethyl ether (diglyme), triethylene glycol dimethyl ether (triglyme) and mixtures containing at least two of these above-stated polyethers.

The quantity ratio of halosubstituted organic compound to reaction medium may vary widely. The quantity ratio which is optimum in each case may, where necessary, be determined by the person skilled in the art with the assistance of simple preliminary testing.

For a good yield of a Grignard compound produced according to the invention, it is advantageous for the reaction medium used to comprise no or at least the smallest possible amounts of oxygen, carbon dioxide and moisture. These gases are therefore preferably removed from the respective reaction medium and/or said medium is dried using conventional methods known to the person skilled in the art prior to the reaction.

With the process according to the invention, various halosubstituted organic compounds may be reacted simultaneously with the magnesium. Preferably only one halosubstituted-organic compound is reacted in each case with the process according to the invention.

In addition, it goes without saying that, in the process according to the invention, it is possible to use not only organic compounds which comprise one halogen atom as substituent, but also those which are substituted with two or more optionally different halogen atoms.

The halosubstituted organic compounds preferably used for the reaction according to the invention are aliphatic halogen compounds, cycloaliphatic halogen compounds optionally comprising at least one heteroatom in the ring system or aromatic halogen compounds optionally comprising at least one heteroatom in the ring system.

Possible saturated or unsaturated aliphatic halogen compounds are those compounds which comprise 1 to 10 carbon atoms, particularly preferably 1 to 5 carbon atoms and very particularly preferably 1 to 3 carbon atoms. Preferred cycloaliphatic halogen compounds, which optionally comprise at least one heteroatom in the ring system, are those with 3 to 8 carbon atoms.

These halogen compounds may be substituted with fluorine, chlorine, bromine or iodine, preferably with chlorine, bromine or iodine, particularly preferably with bromine or iodine.

Suitable aromatic halogen compounds are preferably compounds of the general formulae I or II

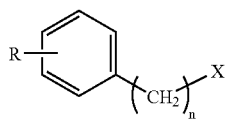

(I)

with n=1, 2 or 3

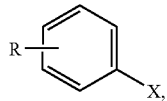

(II)

in which X in each case denotes F, Cl, Br or I, preferably Cl, Br or I, particularly preferably Br or I, and the substituent R is selected from the group consisting of F, Cl, Br, I, a $C_{1-5}$ alkyl residue optionally at least mono-substituted with fluorine, a $C_{1-5}$ alkoxy residue, an $NO_2$ residue, an $N(R^1)_2$ residue, a $CON(R^1)_2$ residue, an $SR^1$ residue, an $SOR^1$ residue, an $SO_2R^1$ residue, an $SO_2N(R^1)_2$ residue, a residue of the general formulae III to VI

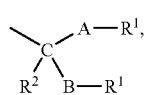

(III)

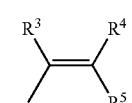

(IV)

(V)

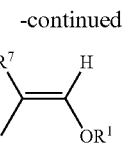

(VI)

and an aryl or heteroaryl residue, which may optionally be at least mono-substituted with R', wherein A and B, identical or different, denote O, S or NH, and preferably both denote O, the residue $R^1$ in each case denotes a $C_{1-6}$ alkyl residue, preferably a $C_{1-3}$ alkyl residue, particularly preferably a methyl or ethyl residue or—in the case of the general formula III—the two residues $R^1$ as ring members mean the group $CH_2$—$CH_2$ or $CH_2$—$CH_2$—$CH_2$, the residues $R^2$, $R^3$, $R^4$, $R^5$, $R^6$ and $R^7$, in each case mutually independently, denote H, a $C_{1-6}$ alkyl residue, preferably a $C_{1-3}$ alkyl residue, particularly preferably a methyl or ethyl residue, or an optionally substituted aryl residue and/or an aryl residue optionally comprising at least one heteroatom, preferably an optionally substituted phenyl residue, particularly preferably an unsubstituted phenyl residue, and R' is selected from the group consisting of F, Cl, Br, I, a $C_{1-5}$ alkyl residue optionally at least mono-substituted with fluorine, a $C_{1-5}$ alkoxy residue, an $NO_2$ residue, an $N(R^1)_2$ residue, a $CON(R^1)_2$ residue, an $SR^1$ residue, an $SOR^1$ residue, an $SO_2R^1$ residue, an $SO_2N(R^1)_2$ residue and a residue of the above-stated general formulae III to VI.

If one of the above-stated cycloaliphatic or aromatic halogen compounds comprises at least one heteroatom in the ring system, this may preferably be selected from the group consisting of oxygen, sulfur and nitrogen.

If a compound of the general formula II is used as aromatic halogen compound, o-bromoanisole, m-bromoanisole, p-bromoanisole, o-bromobenzotrifluoride, m-bromobenzotrifluoride or p-bromobenzotrifluoride, particularly preferably m-bromoanisole, is suitable for the reaction according to the invention.

The molar ratio of magnesium to halosubstituted organic compound may vary. The magnesium and the halosubstituted organic compound are preferably used in equimolar quantities, because the yield of desired Grignard compound is conventionally achieved thereby.

The process according to the invention may proceed under the protective gas conditions known to the person skilled in the art and conventional for the production of Grignard compounds. The protective gas atmosphere is preferably an atmosphere of argon and/or nitrogen, as described for example in "Grignard Reagents New Developments", Herman G. Richey Jr., John Wiley and Sons Ltd, 2000, pages 185 to 275. The corresponding literature description is hereby introduced as a reference and is deemed to be part of the disclosure.

According to the invention, the power with which the microwaves are irradiated, and the frequency of the irradiated microwaves may likewise vary over a wide range.

The microwave irradiation preferably proceeds at a power of 100 to 1200 watt, particularly preferably 100 to 250 watt.

The frequency of the irradiated microwaves is preferably in the range of 850 to 22250 MHz, particularly preferably in the range of 915±25 MHz, 2450±13 MHz, 5800±75 MHz or 22125±125 MHz.

The duration of the reaction for performing the process according to the invention may vary as a function of a plurality of parameters, for example the type of halosubstituted organic compound, the type of reaction medium and/or the reaction temperature. The duration of the reaction which is in each case optimum may be determined by the person skilled in the art by simple preliminary testing.

The duration of the reaction preferably amounts, in the process according to the invention, to no more than 60 minutes, particularly preferably no more than 45 minutes and very particularly preferably no more than 30 minutes.

In a preferred embodiment of the process according to the invention, the reaction proceeds at a temperature of up to at most the boiling temperature of the liquid reaction medium. The reaction is preferably performed with refluxing of the liquid reaction medium.

The time at which irradiation of the microwaves for the reaction begins and the duration of microwave irradiation may likewise vary.

Thus, it is possible, for example, to begin microwave irradiation only once all the reaction components have been added to the reaction medium. Alternatively, the magnesium may for example be initially present in the reaction medium, part of the halosubstituted organic compound may be added, then microwave irradiation may be started and then the remainder of the halosubstituted organic compound may further be added.

Microwave irradiation may for example proceed only up to the start of the reaction of the magnesium with the halosubstituted organic compound, so-called activation of the reaction, or during the entire reaction.

With the process according to the invention, Grignard compounds may be produced in a very good yield and within short reaction times. The Grignard compounds obtained using the process according to the invention are further distinguished by high purity, such that they are very well suited to the production of chemical compounds which conventionally should not be subjected to any further purification step after production, such as for example substance libraries produced using combinatorial chemistry.

The invention is explained below with reference to Examples. These explanations are given merely by way of example and do not restrict the general concept of the invention.

EXAMPLES

The chemicals and reaction media used were purchased from conventional suppliers (Acros, Aldrich, Fluka, Lancaster, Merck).

The gas chromatography analyses were performed with an HP 6890 gas chromatograph with a PTV (Programmed Temperature Vaporization (Inlet)) injector and a 5973 mass selective detector (Hewlett-Packard, now Agilent Technologies Deutschland GmbH, Hewlett-Packard-Straße 8, 76337 Waldbronn) coupled thereto or with a GC 17 A gas chromatograph (Shimadzu Deutschland GmbH, Albert-Hahn-Straße 6 bis 10, 47269 Duisburg).

Example 1a

Production of Grignard Compound from m-bromoanisole

In a microwave device of the type MLS ETHOS 600 (MLS-GmbH, Auenweg 37, 88299 Leutkirch, Germany), an apparatus was constructed which consisted of a 250 ml two-necked flask with a temperature sensor and a 40 cm long dip tube, onto which were fitted a two-necked attachment with a dropping funnel with pressure equalization and a jacketed reflux condenser together with an inlet for protective gas.

50 mmol of magnesium chips in 20 ml of dried, nitrogen-bubbled tetrahydrofuran were then introduced into the two-necked flask and the apparatus was provided with a nitrogen atmosphere. Under 250 watt microwave irradiation, 1 g of m-bromoanisole (corresponding 10 wt. % of the total quantity of m-bromoanisole) was added dropwise. The mixture obtained in this way was then further irradiated with microwaves at a power of 100 watt. After activation of the reaction—the reaction medium became turbid—the remaining quantity of the m-bromoanisole was added dropwise and irradiation with microwaves was continued at a power of 100 watt.

At intervals of in each case five minutes, beginning once addition of all the m-bromoanisole was complete, samples were taken with a syringe, which were then introduced into a saturated ammonium chloride solution for hydrolysis of the Grignard compound produced. The aqueous solution thus obtained was then extracted with the assistance of diethyl ether and analysed by gas chromatography, optionally in combination with mass spectrometry. This analysis provides information about the content of Grignard compound produced, unreacted halogen compound and undesired secondary products.

The determined quantities of the anisole produced by hydrolysis of the Grignard compound, unreacted m-bromoanisole and the quantity of undesired secondary products are reproduced in Table 1a below:

TABLE 1a

| Duration of reaction in minutes | % Anisole | % m-Bromoanisole | % Secondary products |
|---|---|---|---|
| 5 | 66 | 23 | 11 |
| 10 | 78 | 12 | 10 |
| 15 | 89 | 7 | 4 |

Example 1b

Production of Grignard Compound from m-bromoanisole

The structure, procedure and analysis were as set out under Example 1a. At variance with Example 1a, microwave irradiation proceeded only once addition of the entire quantity of m-bromoanisole was complete. The duration of microwave irradiation was 30 minutes at a power of 100 watt.

The determined quantities of anisole produced by hydrolysis of the Grignard compound, unreacted m-bromoanisole and the quantity of undesired secondary products are reproduced in Table 1b below:

TABLE 1b

| Duration of reaction in minutes | % Anisole | % m-Bromoanisole | % Secondary products |
|---|---|---|---|
| 5 | 80 | 15 | 5 |
| 10 | 93 | 6 | 1 |
| 15 | 96 | 4 | — |
| 20 | 96 | 4 | — |
| 25 | 99 | 1 | — |

Example 1c)

Production of Grignard Compound from m-bromoanisole

The structure, procedure and analysis were as set out under Example 1a. At variance with Example 1a, 100 watt microwave irradiation proceeded only until activation of the reaction. Stirring was then continued for 30 minutes at room temperature.

The determined quantities of anisole produced by hydrolysis of the Grignard compound, unreacted m-bromoanisole and the quantity of undesired secondary products are reproduced in Table 1c below:

TABLE 1c

| Duration of reaction in minutes | % Anisole | % m-Bromoanisole | % Secondary products |
|---|---|---|---|
| 28 | 88 | 12 | — |

Example 2

Production of Grignard Compound from m-bromoanisole

The structure, procedure and analysis were as set out under Example 1a. At variance with Example. 1a, 20 ml of dried dioxane were used as reaction medium. The determined quantities of the anisole produced by hydrolysis of the Grignard compound, unreacted m-bromoanisole and the quantity of undesired secondary products are reproduced in Table 2 below:

Comparative Example 1

Production of Grignard Compound from m-bromoanisole without Microwave Irradiation 50 mmol of magnesium chips in dried dioxane were introduced under a nitrogen atmosphere into a 250 ml three-necked flask with jacketed coil condenser, dropping funnel with pressure equalization and protective gas inlet and outlet, 9.56 g (50 mmol) of m-bromoanisole were added dropwise and refluxing was performed for three hours once addition of the m-bromoanisole was complete.

The reaction mixture was analysed in accordance with Example 1a.

The determined quantities of the anisole produced by hydrolysis of the Grignard compound, unreacted m-bromoanisole and the quantity of undesired secondary products are reproduced in Table 2 below:

TABLE 2

| Duration of reaction | % Anisole | % m-Bromoanisole | % Secondary products |
|---|---|---|---|
| Example 2 | | | |
| 25 minutes | 96 | 2 | 2 |
| Comparative Example 1 | | | |
| 180 minutes | No reaction | | |

While the Grignard compound was produced from m-bromoanisole using the process according to the invention in a very short reaction time with a very good yield and very good purity, production using the conventional process for the production of Grignard compounds does not result in any reaction between the reaction components.

Example 3

Production of Grignard Compound from m-bromobenzotrifluoride

The procedure was as described for Example 1b. At variance therewith, m-bromobenzotrifluoride was used as halosubstituted organic compound. The duration of microwave irradiation was 55 minutes at a power of 100 to 150 watt.

The determined quantity of the benzotrifluoride produced by hydrolysis of the Grignard compound, unreacted m-bromoanisole and the quantity of undesired secondary products are reproduced in Table 3 below.

Comparative Example 2

The procedure was as described for Comparative Example 1. At variance therewith, m-bromobenzotrifluoride was used as halosubstituted organic compound.

The determined quantity of the benzotrifluoride produced by hydrolysis of the Grignard compound, unreacted m-bromoanisole and the quantity of undesired secondary products are reproduced in Table 3 below.

TABLE 3

| Duration of reaction in minutes | % Benzotrifluoride | % m-Bromobenzotrifluoride | % Secondary products |
|---|---|---|---|
| Example 3 | | | |
| 5 | 74 | 26 | — |
| 10 | 69 | 31 | — |
| 15 | 71 | 29 | — |
| 30 | 50 | 42 | 8 |
| 40 | 34 | 52 | 14 |
| 55 | 34 | 52 | 14 |
| Comparative Example 2 | | | |
| 180 minutes | 31 | 33 | 36 |

In addition to an improvement in the yield of desired Grignard compound, production using the process according to the invention results in a smaller quantity of undesired secondary products.

Example 4

Production of the Grignard Compound from p-chlorobenzylchloride

The procedure was as described for Example 1b. At variance therewith, p-chlorobenzylchloride was used as halosubstituted organic compound and dried diethyl ether was used as reaction medium. The duration of microwave irradiation was 15 minutes at a power of 100 to 150 watt.

The determined quantity of the benzylchloride produced by hydrolysis of the Grignard compound, unreacted p-chlorobenzylchloride and the quantity of undesired secondary products are reproduced in Table 4 below.

Comparative Example 3

The procedure was as described for Comparative Example 1. At variance therewith, p-chlorobenzylchloride was used as halosubstituted organic compound and dried diethyl ether was used as reaction medium.

The determined quantity of the benzylchloride produced by hydrolysis of the Grignard compound, unreacted p-chlorobenzylchloride and the quantity of undesired secondary products are reproduced in Table 4 below.

TABLE 4

| Duration of reaction in minutes | % Benzyl-chloride | p-Chlorobenzyl-chloride | % Secondary products |
|---|---|---|---|
| Example 4 | | | |
| 5 | 59 | 20 | 21 |
| 10 | 62 | 9 | 29 |
| 15 | 72 | 3 | 25 |
| Comparative Example 3 | | | |
| 180 minutes | 45 | 31 | 24 |

With an unchanged content of secondary products, an excellent yield of the desired Grignard compound may be obtained within a substantially shorter reaction time.

The invention claimed is:

1. A process for producing at least one Grignard compound, said process comprising reacting magnesium in a liquid reaction medium under a protective gas atmosphere with microwave irradiation with at least one aromatic halogen compound of the formulae I or II:

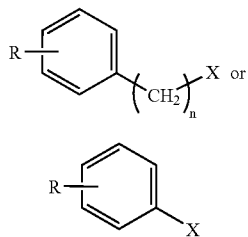

in which
n in formula I represents 1, 2 or 3;
X in formulae I and II represents F, Cl, Br or I; and
R in formulae I and II represents a member selected from the group consisting of F, Cl, Br, I, $C_{1-5}$-alkyl optionally at least mono-substituted with F, $C_{1-5}$-alkoxy, $NO_2$, $N(R^1)_2$, $CON(R^1)_2$, $SR^1$, $SOR^1$, $SO_2R^1$, $SO_2N(R^1)_2$, a group of the Formula III to VI:

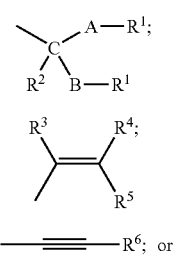

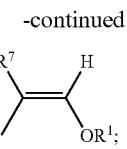

and an aryl or heteroaryl group, which is optionally at least mono-substituted with R';
wherein
A and B are identical or different and represent O, S or NH;
$R^1$ represents in each case $C_{1-6}$-alkyl; or in formula III the two $R^1$ groups optionally combine to form —$CH_2$—$CH_2$— or —$CH_2$—$CH_2$—$CH_2$—;
$R^2$, $R^3$, $R^4$, $R^5$, $R^6$ and $R^7$ independently represent H, $C_{1-6}$-alkyl, optionally substituted aryl or optionally substituted heteroaryl; and
R' represents F, Cl, Br, I, $C_{1-5}$-alkyl optionally at least mono-substituted with F, $C_{1-5}$-alkoxy, $NO_2$, $N(R^1)_2$, $CON(R^1)_2$, $SR^1$, $SOR^1$, $SO_2R^1$, $SO_2N(R')_2$, or a group of the Formula III to VI.

2. A process according to claim 1, wherein the magnesium is present in the form of magnesium strip or in multiparticulate form.

3. A process according to claim 1, wherein the reaction medium is at least one ether compound or a mixture containing at least one ether compound.

4. A process according to claim 3, wherein the at least one ether compound is selected from the group consisting of aliphatic ethers, cyclic ethers and aliphatic polyethers.

5. A process according to claim 4, wherein the at least one ether compound is at least one dialkyl ether.

6. A process according to claim 4, wherein the at least one ether compound is tetrahydrofuran, 1,4-dioxane or a mixture thereof.

7. A process according to claim 4, wherein the at least one ether compound is an aliphatic polyether based on an alkylene glycol.

8. A process according to claim 7, wherein the polyether is selected from the group consisting of ethylene glycol dimethyl ether (monoglyme), diethylene glycol dimethyl ether (diglyme), triethylene glycol dimethyl ether (triglyme) and mixtures containing at least two of these polyethers.

9. A process according to claim 1, wherein X denotes Cl, Br or I.

10. A process according to claim 1, wherein the group $R^1$ denotes a $C_{1-3}$ alkyl group.

11. A process according to claim 1, wherein the groups $R^2$, $R^3$, $R^4$, $R^5$, $R^6$ and $R^7$, in each case mutually independently, denote a $C_{1-3}$ alkyl group, or an optionally substituted phenyl group.

12. A process according to claim 1, wherein A and B in each case denote O.

13. A process according to claim 1, wherein the compound of formula II is selected from the group consisting of o-bromoanisole, m-bromoanisole, p-bromoanisole, o-bromobenzotrifluoride, m-bromobenzotrifluoride and p-bromobenzotrifluoride.

14. A process according to claim 1, wherein p-chlorobenzylchloride is used as compound of formula I.

15. A process according to claim 1, wherein the magnesium and the at least one aromatic halogen compound(s) are used in equimolar quantities.

16. A process according to claim 1, wherein the protective gas atmosphere is an atmosphere of argon and/or nitrogen.

17. A process according to claim 1, wherein microwave irradiation proceeds at a power of 100 to 1200 watt.

18. A process according to claim 1, wherein irradiation is performed with microwaves of a frequency in the range of 850 to 2250 MHz.

19. A process according to claim 1, wherein the duration of the reaction amounts to no more than 60 minutes.

20. A process according to claim 1, wherein the reaction proceeds at a temperature of up to at most the boiling temperature of the liquid reaction medium.

21. A process according to claim 20, wherein the reaction proceeds with refluxing of the liquid reaction.

22. A process according to claim 2, where the magnesium is multiparticulate in the form of chips or powder.

23. A process according to claim 5, where the at least one dialkyl ether is diethyl ether, dibutyl ether or a mixture thereof.

24. A process according to claim 7, where the aliphatic polyether is based on ethylene glycol.

25. A process according to claim 12, where the group $R^1$ in each case denotes a $C_{1-3}$ alkyl group.

26. A process according to claim 12, where the group $R^1$ in each case denotes a methyl or ethyl group.

27. A process according to claim 9, where X denotes Br or I.

28. A process according to claim 10, where the group $R^1$ denotes a methyl or ethyl group.

29. A process according to claim 11, where the groups $R^2$, $R^3$, $R^4$, $R^5$, $R^6$ and $R^7$, in each case mutually independently, denote a methyl or ethyl group, or an unsubstituted phenyl residue.

30. A process according to claim 13, where the compound of the formula II is m-bromoanisole.

31. A process according to claim 17, where the microwave irradiation proceeds at a power of 100 to 250 watts.

32. A process according to claim 18, where the irradiation is performed with microwaves of a frequency in the range selected from the group consisting of 915±25 MHz, 2450±13 MHz, 5800±75 MHz and 22125±125 MHz.

33. A process according to claim 19, where the duration of the reaction amounts to no more than 45 minutes.

34. A process according to claim 19, where the duration of the reaction amounts to no more than 30 minutes.

\* \* \* \* \*